United States Patent

Himmler et al.

[11] Patent Number: 5,102,971
[45] Date of Patent: Apr. 7, 1992

[54] SOLUBLE POLYAROMATIC COMPOUNDS

[75] Inventors: Thomas Himmler, Cologne; Rudolf Braden, Odenthal-Scheuren; Joachim Genz, Krefeld; Karsten-Josef Idel, Krefeld; Ralf Pakull, Krefeld, all of Fed. Rep. of Germany

[73] Assignee: Bayer Aktiengesellschaft, Leverkusen-Bayerwerk, Fed. Rep. of Germany

[21] Appl. No.: 582,794

[22] Filed: Sep. 14, 1990

Related U.S. Application Data

[63] Continuation of Ser. No. 367,368, Jun. 14, 1989, abandoned.

[30] Foreign Application Priority Data

Jun. 25, 1988 [DE] Fed. Rep. of Germany ....... 3821567

[51] Int. Cl.⁵ ............................... C08G 79/02
[52] U.S. Cl. .................... 528/167; 528/171; 528/173; 528/174; 528/271; 528/274; 528/275; 528/280; 528/281; 528/287; 528/288; 528/293; 528/367; 528/370; 528/373; 528/398; 528/400; 528/401; 524/126; 524/233; 524/319; 524/327; 524/413; 524/414; 524/431; 524/432
[58] Field of Search .............. 528/167, 171, 173, 174, 528/271, 274, 275, 280, 281, 287, 288, 293, 367, 370, 373, 398, 400, 401; 524/126, 233, 319, 327, 413, 414, 431, 432, 433

[56] References Cited

U.S. PATENT DOCUMENTS

| | | | |
|---|---|---|---|
| 4,326,989 | 4/1982 | Colon et al. | 252/429 |
| 4,400,499 | 8/1983 | Colon | 528/174 |
| 4,521,589 | 6/1985 | Yamamoto et al. | 528/380 |
| 4,870,153 | 9/1989 | Matzner et al. | 528/125 |

FOREIGN PATENT DOCUMENTS 0012201 6/1980 European Pat. Off. .
0131936 1/1985 European Pat. Off. .

OTHER PUBLICATIONS

Bulletin of the Chemical Society of Japan, Yamamoto et al., 1978.
Macromolecular Chemistry, Yamamoto et al., 1985.

Primary Examiner—John Kight, III
Assistant Examiner—S. A. Acquah
Attorney, Agent, or Firm—Connolly & Hutz

[57] ABSTRACT

Process for the preparation of polyaromatic compounds in which an aromatic dichloro compound, optionally in the presence of an anhydrous aprotic solvent, is reacted with metallic zinc, manganese or magnesium in the presence of a catalyst system of
(1) from 0.1 to 25 mol-% (based on the dihalogen compound) of a nickel salt, nickel complex salt or nickel complex,
(2) from 2 to 100 mol per mol of nickel in (1) of a triarylphosphine and optionally
(3) from 0.1 to 10 mol per mol of nickel (1) of a halide, sulphate or phosphate of an alkali metal, alkaline earth metal, zinc, magnesium or manganese.

1 Claim, No Drawings

SOLUBLE POLYAROMATIC COMPOUNDS

This application is a continuation of application Ser. No. 07/367,368, filed 6/14/89, now abandoned.

Polyaromatic compounds have acquired a position of interest on account of their thermal stability and potential electric conductivity.

The best known method for their preparation is the polymerisation of benzenes and certain substituted benzenes in the presence of Lewis acids, a cocatalyst and an oxidizing agent (J. Polym. Sci. Part D (Macromolecular Reviews) 5 (1971) 385 to 430). The properties of the products depend to a great extent on the catalyst used.

Other methods for the preparation of polyarylenes are the Wurtz-Fittig reaction, in which e.g. p-dichlorobenzene is reacted with metallic sodium or sodium-potassium alloys, and the Ullmann synthesis, in which dibromo- or preferably diiodoaryl compounds are polymerised by the action of metallic copper.

Another possible method lies in the polymerisation of mono-Grignard compounds of dihalogenated aromatic compounds catalysed by transition metals, e.g. the polymerisation of p-dibromobenzene with magnesium in the presence of 2,2'-bipyridyl-nickel (II) chloride (Japanese Patent Application 52-154 900) and the polymerisation of 1,4-dibromonaphthalene with magnesium in the presence of nickel (II) acetylacetonate as catalyst (Makromol. Chem. 184 (1983) 2241 to 2249).

This process may also be used for the preparation of polyhetarylenes such as polythiophenes (U.S. Pat. No. 4,521,589).

This method can in most cases only be carried out with dibromo compounds as starting materials. Since Grignard compounds occur as intermediate products, the possibility of using substituted starting materials is very limited. The method is therefore not universally applicable.

In some cases, the magnesium may be replaced by metallic zinc. Thus it is known to polymerise 2,5-dibromothiophene and 1,4-diiodobenzene with metallic zinc in the presence of palladium or nickel catalysts (Makromol. Chem., Rapid Commun. 6 (1985) 671 to 674). This process is, however, virtually limited to aromatic diiodo and dibromo compounds as starting materials. Dichloroaromatic compounds generally cannot be reacted by this process. The only known reaction of this kind with aromatic dichloro compounds is the reaction of 4,4'-dichlorobenzophenone with bis-(diphenylphosphino)ethane nickel (II) chloride, but this reaction proceeds very slowly and requires a catalyst which is difficult to obtain.

No simple, generally applicable method for the preparation of substituted polyarylenes from readily accessible starting materials has therefore hitherto been known.

The present invention relates to a process for the preparation of polyaromatic compounds, wherein an aromatic dichloro compound, which can be substituted but not with acidic substituents or nitro groups, is reacted with metallic zinc, manganese or magnesium, optionally in the presence of an anhydrous aprotic solvent, and in the presence of a catalyst system of (1) from 0.1 to 25 mol-% (based on the dihalogen compound) of a nickel salt, nickel complex salt or nickel complex,
(2) from 2 to 100 mol per mol of nickel in (1) of a triarylphosphine and optionally
(3) from 0.1 to 10 mol per mol of nickel (1) of a halide, sulphate or phosphate of an alkali metal, alkaline earth metal, zinc, magnesium or manganese as promoter at temperatures from 0° to 250° C. and the polyaromatic compound obtained is isolated.

The process is preferably employed for the preparation of polyaromatic compounds containing recurrent structural units of the following formula

wherein n stands for a number from 3 to 1000 and A stands for an aromatic group corresponding to the following formula

or a group of the following formula

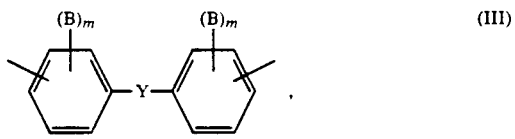

one to three CH units in the aromatic rings of the formulae (II) and (III) being optionally replaced by nitrogen atoms,
in which formula,
Y=CO, COO, CONR$^1$ wherein R$^1$=hydrogen, C$_1$-C$_6$-alkyl or C$_6$-C$_{10}$-aryl, SO, SO$_2$ or

wherein n=1 to 6, W=C, or Si and R$^2$ and R$^3$ denote, independently of one another, hydrogen, C$_1$-C$_6$-alkyl (optionally mono- or multi-substituted by halogen, preferably by fluorine); C$_6$-C$_{10}$-aryl (optionally mono- or multi-substituted by halogen, preferably fluorine), or halogen, (preferably fluorine);
oxygen or
NR$^4$ wherein R$^4$ stands for hydrogen, C$_1$-C$_6$-alkyl or C$_6$-C$_{10}$-aryl;
or a heterocyclic group of the following formula

wherein
B=hydrogen,
C$_1$-C$_{18}$-alkyl or C$_6$-C$_{14}$-aryl, either of which may be mono- or multisubstituted by halogen (preferably by fluorine), or by alkoxy, cyano or dialkylamino, $C_1$-$C_6$-alkoxy,
fluoroalkyl containing one or two carbon atoms and 1 to 5 fluorine atoms,

| | |
|---|---|
| COO—$C_1$-$C_{18}$-alkyl or -cycloalkyl or COO—$C_6$-$C_{10}$-aryl. | any of which may be mono- or multisubstituted by halogen, (preferably fluorine) or by alkoxy, cyano or dialkylamino. | fluoroalkoxy containing one or two carbon atoms and one to five fluorine atoms,
substituted or unsubstituted phenoxy,
$C_2$-$C_{16}$-dialkylamino,
$C_6$-$C_{12}$-diarylamino,
diacetylamino,
formyl,
cyano,

| | |
|---|---|
| CO—$C_1$-$C_6$-alkyl, CO—$C_6$-$C_{10}$-aryl, OCO—$C_1$-$C_{18}$-alkyl or OCO—$C_6$-$C_{10}$-aryl | any of which are optionally mono- or multisubstituted by halogen, (preferably fluorine). |

$CONR^5R^6$ wherein $R^5$ and $R^6$ denote, independently of one another, $C_1$-$C_{18}$-alkyl or $C_6$-$C_{10}$-aryl,

| | |
|---|---|
| $C_1$-$C_{18}$-alkylsulphinyl, $C_6$-$C_{18}$-arylsulphinyl, $C_1$-$C_{18}$-alkylsulphonyl and $C_6$-$C_{10}$-arylsulphonyl | any of which may be mono- or multisubstituted by halogen, preferably fluorine). |

Q=S or NR wherein R=$C_1$-$C_{18}$-alkyl, benzyl, substituted or unsubstituted phenyl, formyl or acetyl,
m=1 or 2 and if
m=2 then
both groups B may together denote
—CH=CH—CH=CH—,
—CH=CH—CH$_2$—,
—CH$_2$CH$_2$CH$_2$—,
—CH$_2$CH$_2$CH$_2$CH$_2$—,
—OCH$_2$O—,
—OCH$_2$CH$_2$O—,
any of which may be mono- or multisubstituted by halogen, (preferably fluorine),
wherein a dichloro compound corresponding to the following formula Cl—A—Cl       (V)

wherein A has the meaning indicated above is reacted with metallic zinc, manganese or magnesium, optionally in the presence of an anhydrous aprotic solvent, in the presence of a catalyst system of
(1) from 0.1 to 25 mol-% (based on the dihalogen compound) of a nickel salt, nickel complex salt or nickel complex,
(2) from 2 to 100 mol per mol of nickel in (1) of a triaryl phosphene and optionally
(3) from 0.1 to 10 mol per mol of nickel in (1) of a halide, sulphate or phosphate of an alkali metal, alkaline earth metal, zinc, magnesium or manganese
at temperatures from 0° to 250° C. and the polyaromatic compound formed is isolated.

The invention further relates to polyaromatic compounds corresponding to formula (I) wherein n stands for a number from 3 to 1000 and A stands for an aromatic group corresponding to the following formula

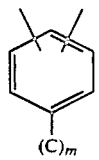

(VII)

or a group for the following formula

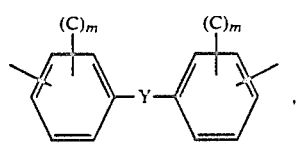

(VIII)

in which formulae (VII) and (VIII) one to three of the CH units in the aromatic rings may be replaced by nitrogen atoms, and
Y=CO, COO, CONR$^1$ wherein R$^1$=hydrogen, $C_1$-$C_6$-alkyl or $C_6$-$C_{10}$-aryl, SO, SO$_2$,

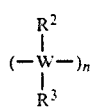

wherein
n=1 to 6,
W=C or Si and
R$^2$ and R$^3$ denote, independently of one another, hydrogen, $C_1$-$C_6$-alkyl optionally mono- or multi-substituted by halogen (preferably fluorine); $C_6$-$C_{10}$-aryl, optionally mono- or multisubstituted by halogen (preferably by fluorine); and halogen, (preferably fluorine);
oxygen or
NR$^4$ wherein R$^4$=hydrogen, $C_1$-$C_6$-alkyl or $C_6$-$C_{10}$-aryl and

| | |
|---|---|
| C = COO—$C_1$-$C_{18}$-alkyl or -cycloalkyl or COO—$C_6$-$C_{10}$-aryl | optionally mono- or multi-substituted by halogen, (preferably fluorine). | a substituted or unsubstituted phenoxy, $C_2$-$C_{16}$-dialkylamino, $C_6$-$C_{12}$-diarylamino, diacetylamino, formyl, cyano,

| | |
|---|---|
| CO—$C_1$-$C_6$-alkyl, CO—$C_6$-$C_{10}$-aryl, OCO—$C_1$-$C_{18}$-alkyl or OCO—$C_6$-$C_{10}$-aryl | any of which may be mono- or multisubstituted by halogen (preferably fluorine), |

$CONR^5R^6$ wherein $R^5$ and $R^6$ denote, independently of one another, $C_1$-$C_{18}$-alkyl or $C_6$-$C_{10}$-aryl,

| | |
|---|---|
| $C_1$-$C_{18}$-alkylsulphinyl, $C_6$-$C_{10}$-arylsulphinyl, $C_1$-$C_{18}$-alkylsulphonyl or $C_6$-$C_{10}$-arylsulphonyl | any of which are optionally mono- or multisubstituted by halogen (preferably fluorine). | m = 1 or 2 and if m = 2, the two groups C may also together denote OCH$_2$O or OCH$_2$CH$_2$O optionally mono- or multisubstituted by halogen (preferably fluorine).

The catalyst system used in the process according to the invention contains a nickel compound which is preferably anhydrous, a ligand selected from triarylphosphines having 6 to 10 carbon atoms in each aryl unit, optionally a promoter selected from halides, sulphates or phosphates of an alkali metal, alkaline earth metal, manganese or zinc, and a metal such as zinc, manganese or magnesium. A polycyclic aromatic compound having at least two nitrogen atoms in different aromatic rings and 10 to 18 carbon atoms may optionally be used as additional component.

Suitable anhydrous nickel compounds are those which may be reduced by the above-mentioned metals or are already in a reduced form. The following are mentioned here without any claim to completeness: Nickel(II) halides such as nickel(II) chloride, bromide and iodide, nickel(II) sulphate, nickel(II) carbonate, nickel(II) salts of organic acids having 1 to 18 carbon atoms, nickel(II) complexes such as nickel acetyl acetonate and dichloro-bis-(triphenylphosphine)-nickel(II) and nickel(O) complexes such as bis-(cycloocta-1,5-diene)-nickel(O) or tetrakis-(triphenylphosphine)-nickel(O) which may be prepared by processes known in the literature. The above-mentioned nickel(II) halides are preferred, especially nickel(II) chloride, which may be obtained in anhydrous form in known manner, e.g. by reaction of the hexahydrate with thionyl chloride.

The nickel catalyst is used in a quantity of from 0.1 to 25 mol-%, based on the quantity of dichloroaryl compound used, preferably from 1 to 20 mol-%, most preferably from 3 to 15 mol-%.

Suitable triarylphosphines are e.g. triphenylphosphine, the tritolylphosphines and the trinaphthylphosphines. Triphenylphosphine is particularly preferred.

The triarylphosphine is used in a molar ratio to the nickel compound of from 2 to 100, preferably from 4 to 50, most preferably from 5 to 10.

The promoters used are preferably alkali metal halides, alkaline earth metal halides, zinc halides, magnesium halides and manganese halides. The iodides are particularly preferred.

The quantity of promoter may be from 0.1 to 1000 mol-%, based on the quantity of nickel catalyst used, quantities from 1 to 700 mol-% being preferred, especially from 10 to 500 mol-%.

2,2'-Bipyridyl and 1,10-phenanthroline are preferred polycyclic aromatic compounds containing at least two nitrogen atoms. These are preferably used in proportions of 50 to 500 mol-%, based on the quantity of nickel catalyst used.

The metals used may be zinc, manganese or magnesium. Zinc is preferred. The zinc may be used, for example, as zinc dust which may previously have been purified by washing with glacial acetic acid, water and acetone followed by drying in a vacuum.

The metal may be used in a subequivalent quantity but it is preferably used in a quantity of at least one gram atom of metal per mol of dichloro compound and is most preferably used in an excess of up to 10 equivalents.

The reaction may be carried out with or without solvent.

The solvents used for the process according to the invention may be aprotic polar solvents such as dimethylformamide, dimethylacetamide, N-methyl-caprolactam, N-methyl-pyrrolidine, dimethylsulphoxide, tetramethylene sulphone, etc. The solvents are dried in known manner before use and distilled under a protective gas, e.g. nitrogen.

The reaction may be carried out at temperatures from 0° to 250° C., preferably from 20° to 200° C., most preferably from 50° to 150° C.

The coupling reaction is advantageously carried out in an inert protective gas atmosphere such as helium, argon or nitrogen.

The reaction is generally carried out at normal pressure but may be carried out at elevated or reduced pressure.

The reaction time is from 0.05 to 24 hours, preferably from 0.1 to 10 hours, most preferably from 0.5 to 8 hours.

The polyarylenes are used e.g. as high temperatures stable fibres, films and coatings, as modifiers for plastics, as liquid crystalline materials and as precursors for other polymers.

EXAMPLE 1

Polyphenylene 131 g of zinc powder, 15 g of sodium iodide, 131 g of triphenylphosphine and 6.5 g of anhydrous nickel(II) chloride were introduced into 600 ml of absolute dimethylformamide under a nitrogen atmosphere. A deep red brown suspension was obtained after half an hour at 50° to 60° C. A solution of 147 g of p-dichlorobenzene in 100 ml of absolute dimethylformamide was added dropwise to this suspension. After 6 hours at 80° C., 2 l of chloroform were added to the reaction mixture and the mixture was shaken with 1 l of water. The organic phase containing the suspended solid substances was separated off and the solid was filtered off and stirred up with dilute aqueous hydrochloric acid. After the solid has been washed with water and dried, 42 g of polyphenylene corresponding to the following formula were obtained

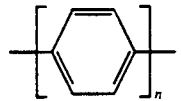

Mp.: >300° C.

The elementary analysis showed the following composition: C 86.95%, H 5.25% Cl 5.6%.

According to the figure above, n was found to be about 16, assuming that both end groups are chlorine.

EXAMPLE 2

Poly-(carboxymethyl)-phenylene 157 g of zinc powder, 262 g of triphenylphosphine, 30 g of sodium iodide and 13 g of anhydrous nickel(II) chloride were introduced into 1.2 l of absolute dimethylformamide under a nitrogen atmosphere. A deep red brown suspension was obtained after half an hour at 50° to 60° C. A solution of 410 g of 2,5-dichlorobenzoic acid methyl ester in 400 ml of absolute dimethylformamide was added dropwise to this suspension. After 6 hours at 80° C., the solvent was distilled off and the residue was dissolved in 5 l of chloroform and vigorously stirred up with 3 l of dilute aqueous hydrochloric acid. After filtration the organic phase was separated and extracted with 2 l of water. About 1 to 2 l of chloroform were distilled off. About 4 l methanol were added to the solution remaining behind. The resulting precipitate was suction filtered and dried. The crude product obtained was ground to a fine powder and then boiled up with 2 to 3 l of acetonitrile for about 2 hours. The suspension was suction filtered while hot and the residue dried. 240 g of poly(carboxymethyl)-phenylene corresponding to the following formula were thus obtained.

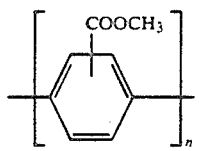

Mp.: >300° C.

The elementary analysis showed the following composition: C 71.15%, H 4.75% Cl 0.50%, O 23.15%.

The figure above shows that n is approximately 100, assuming that both end groups are chlorine.

The experiments shown in Table 1 were carried out analogously to Examples 1 and 2.

TABLE 1

Oligomerisation of dichloroaromatic compounds (5 mol-% Ni; PPh₃: Ni = 10; 200 mol-% NaI, based on the Ni compound; average chain length: 6 h; reaction temperature 80° C.)

| Example | Dichloro compound | Equivalents of Zn | DMF (ml/mol) | Isolated yield (%) | Reaction time n |
|---|---|---|---|---|---|
| 3 | Cl—⌬—O—⌬—Cl | 1.4 | 940 | 27 | 5 |
| 4 | Cl—⌬—C(=O)—⌬—Cl | 1.2 | 1200 | 52 | 3 |
| 5 | Cl—⌬(CH₃)(H₃C)—Cl | 1.2 | 1000 | 21 | 6 |
| 6 | Cl—⌬(i-propyl)(i-propyl)—Cl | 1.2 | 800 | 28 | 3 |
| 7 | Cl—⌬(OCH₃)—Cl | 1.2 | 800 | 39 | 17 |
| 4 | Cl—⌬(COO^tBu)—Cl | 1.2 | 900 | 50 | 75 |
| 9 | Cl—⌬(S)—Cl (thiophene) | 0.75 | 700 | 70 | 22 |

We claim:

1. Polyaromatic polyphenylene compounds corresponding to the formula $$+A+_n \quad (I)$$

wherein n stands for a number from 3 to 1000 and A denotes an aromatic group of the formula

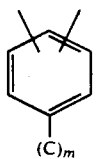

(VII)

in which one to three CH units in each of the aromatic rings can be replaced by nitrogen atoms;

C represents:
  $COO-C_1-C_{18}$-alkyl or -cycloalkyl or $COO-C_6-C_{10}$-aryl, each of which may be unsubstituted or mono or multi substituted by halogen;
  substituted or unsubstituted phenoxy;
  $C_2-C_{16}$-dialkylamino;
  $C_6-C_{12}$-diarylamino;
  diacetylamino;
  formyl;
  cyano;
  $CO-C_1-C_6$-alkyl, $CO-C_6-C_{10}$-aryl, $OCO-C_1-C_{18}$-alkyl or $OCOC_6-C_{10}$-aryl, each of which may be unsubstituted or mono- or multisubstituted by halogen;
  $CONR^5R^6$ wherein $R^5$ and $R^6$ denote, independently of one another, $C_1-C_{18}$-alkyl or $C_6-C_{10}$-aryl;
  $C_1-C_{18}$-alkylsulphinyl, $C_6-C_{10}$-arylsulphinyl, $C_1-C_{18}$-alkylsulphonyl or $C_6-C_{10}$-arylsulphonyl, each of which may be unsubstituted or mono- or multisubstituted by halogen; and m represents the number 1 or 2 and if m represents the number 2, the two groups C together denote $-OCH_2O$ or $-OCH_2CH_2O$, which may be unsubstituted or mono or multisubstituted by halogen.

* * * * *